(12) United States Patent
Brown et al.

(10) Patent No.: US 10,857,269 B2
(45) Date of Patent: Dec. 8, 2020

(54) CASSETTE HAVING AN INTEGRATED FILTER AND BYPASS

(71) Applicant: Fenwal, Inc., Lake Zurich, IL (US)

(72) Inventors: David S. Brown, Lake Barrington, IL (US); Carlos Calderon, Waukegan, IL (US)

(73) Assignee: Fenwal, Inc., Lake Zurich, IL (US)

( * ) Notice: Subject to any disclaimer, the term of this patent is extended or adjusted under 35 U.S.C. 154(b) by 662 days.

(21) Appl. No.: 15/663,218

(22) Filed: Jul. 28, 2017

(65) Prior Publication Data
US 2018/0055986 A1  Mar. 1, 2018

Related U.S. Application Data (60) Provisional application No. 62/378,775, filed on Aug. 24, 2016.

(51) Int. Cl.
| | | |
|---|---|---|
| A61M 1/02 | (2006.01) | |
| A61M 1/34 | (2006.01) | |
| A61M 1/36 | (2006.01) | |
| A61L 2/24 | (2006.01) | |
| A61M 1/30 | (2006.01) | |

(52) U.S. Cl.
CPC ............. *A61M 1/0281* (2013.01); *A61L 2/24* (2013.01); *A61M 1/0218* (2014.02); *A61M 1/0222* (2014.02); *A61M 1/0277* (2014.02); *A61M 1/30* (2013.01); *A61M 1/3496* (2013.01); *A61M 1/3633* (2013.01); *A61M 2205/125* (2013.01); *A61M 2205/128* (2013.01)

(58) Field of Classification Search
CPC .... A61M 1/0218; A61M 1/0222; A61M 1/30; A61M 1/0277; A61M 1/0281; A61M 1/3496; A61M 1/3633; A61M 2205/125; A61M 2205/128
See application file for complete search history.

(56) References Cited

U.S. PATENT DOCUMENTS

| | | |
|---|---|---|
| 5,868,696 A | 2/1999 | Giesler et al. |
| 6,416,293 B1 | 7/2002 | Bouchard et al. |
| 2004/0127841 A1* | 7/2004 | Briggs ................ A61M 1/3681 604/6.01 |
| 2015/0265755 A1 | 9/2015 | Lynn et al. |
| 2015/0265758 A1 | 9/2015 | Verri et al. |
| 2015/0265954 A1 | 9/2015 | Lynn et al. |

FOREIGN PATENT DOCUMENTS

| | | |
|---|---|---|
| GB | 2110564 A | 6/1983 |
| WO | 1998052629 A2 | 11/1998 |
| WO | 2014039086 A1 | 3/2014 |

OTHER PUBLICATIONS

Extended European Search Report for application No. 17184481.4, dated Jan. 10, 2018, 9 pages.

* cited by examiner

*Primary Examiner* — Leslie R Deak
(74) *Attorney, Agent, or Firm* — Cook Alex Ltd.

(57) ABSTRACT

A fluid processing system for controlling fluid flow comprising a cassette comprising defined passageways within a first portion of the cassette and a filter receptacle within a second portion of the cassette, an inlet port in communication with one or more of the defined passageways and an inlet side of the filter receptacle, an outlet port in communication with an outlet side of the filter receptacle, and a filter medium disposed within the filter receptacle between the inlet port and outlet port.

20 Claims, 6 Drawing Sheets

CASSETTE HAVING AN INTEGRATED FILTER AND BYPASS

CROSS-REFERENCE TO RELATED APPLICATIONS

This application claims the benefit of U.S. Provisional Patent App. No. 62/378,775 filed Aug. 24, 2016, which is expressly incorporated herein by reference in its entirety.

FIELD OF THE DISCLOSURE

The present disclosure relates generally to fluid treatment systems and methods and, in particular to a cassette having an integrated filter and bypass for performing biological fluid procedures.

BACKGROUND

The separation of blood into its components is commonly performed in apheresis procedures, in which blood components are separated while a donor or patient is connected to a separation system (sometimes referred to as a "chairside" procedure), or with previously-collected whole blood, in whole blood manufacturing or component processing procedures. For example, a common procedure is the separation of whole blood into plasma and red blood cells.

Such separation procedures may be highly automated, utilizing a single-use fluid circuit comprising containers of various solutions, such as saline, anticoagulant and additive solution, as well as cassettes comprising defined fluid pathways, as well as containers for the receipt of the separated blood components, all of which are interconnected by fluid flow paths in the form of tubing to a separation device, such as a centrifuge or a spinning membrane separator. The fluid circuit is associated with a durable hardware component which has pumps and clamps associated therewith that operatively engage the tubings to circulate the blood and its separated components through the associated single-use fluid circuit. The durable hardware component may include a programmable controller to automatically operate the pumps, clamps and separator in accordance with the desired apheresis procedure.

Before transfusing collected blood components to a recipient in need of a component, or before subjecting blood components to treatment (such as but not limited to pathogen inactivation), it may be desirable to minimize the presence of impurities or other materials that may cause undesired side effects in the recipient. For example, because of possible reactions, it may be desirable to reduce the number of leukocytes in blood components before storage, or at least before transfusion (i.e., "leukoreduction"). Such leukoreduction may be accomplished by flowing the blood components through a leukoreduction filter (also called a leukofilter) that captures white blood cells by requiring passage of the component through a filter medium that retains the undesired leukocytes and other components/ aggregates while allowing the remaining desirable components to pass through the medium and be collected for subsequent transfusion and/or storage. In the case of disposable leukofilters, the used filters may thereafter be discarded.

SUMMARY

According to an exemplary embodiment, the present disclosure is directed to a fluid processing system for controlling fluid flow comprising a cassette comprising defined passageways within a first portion of the cassette and a filter receptacle within a second portion of the cassette, an inlet port in communication with one or more of the defined passageways and an inlet side of the filter receptacle, an outlet port in communication with an outlet side of the filter receptacle, and a filter medium disposed within the filter receptacle between the inlet port and outlet port.

According to an exemplary embodiment, the present disclosure is directed to a fluid processing system for controlling fluid flow, comprising a cassette comprising defined passageways within a first portion of the cassette and a filter receptacle within a second portion of the cassette, an inlet port in communication with one or more of the defined passageways and an inlet side of the filter receptacle, a first outlet port in communication with an outlet side of the filter receptacle, a filter medium disposed within the filter receptacle between the inlet port and the first outlet port, and a bypass passageway in communication with the inlet port and a second outlet port, wherein fluid flowing through the bypass passageway does not make contact with the filter medium.

According to an exemplary embodiment, the present disclosure is directed to a method for transferring fluid through a fluid flow path, comprising providing a cassette comprising defined passageways within a first portion of the cassette and a filter receptacle within a second portion of the cassette, providing an inlet port in communication with one or more of the defined passageways and an inlet side of the filter receptacle, providing a first outlet port in communication with an outlet side of the filter receptacle, providing a filter medium disposed within the filter receptacle between the inlet port and the first outlet port, and providing a bypass passageway in communication with the inlet port and a second outlet port, wherein fluid flowing through the bypass passageway does not make contact with the filter medium.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may allow for a leukofilter to be integrated into one or more cassettes of a disposable fluid circuit.

Some embodiments may reduce the number of tubing segments required to manufacture a disposable fluid circuit.

There have been continuing efforts to automate the apparatus and systems used in the post-collection processing of whole blood, and an automated blood component separator for such post-collection processing may be employed. One class of such automated separators employs relatively rotating surfaces, at least one of which carries a porous membrane. An example of such a membrane separator is disclosed in PCT Patent Application Publication No, WO 2014/039086 A1, which is incorporated by reference in its entirety, although any suitable membrane separator may be used. Another class employs a centrifuge that utilizes centrifugal separation principles. An exemplary centrifugal separator is disclosed in U.S. Pat. No. 5,868,696, which is incorporated by reference in its entirety, although any suitable centrifugal separator may be used.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path.

One component of the disposable circuit that interacts with the pump assembly may be a molded plastic piece commonly referred to as a cassette. As used herein, the term "cassette" refers to a component of a fluid processing system that includes one or more defined fluid passageways. The cassette may be secured to a cassette holder or cassette station of the durable equipment, with a flexible sheeting or diaphragm of the cassette facing the durable equipment. The cassette holder or cassette station may include a number of valve actuators that selectively press against the flexible diaphragm/sheeting for opening and closing valve stations of the cassette, thereby controlling which of the fluid passageways are connected to each other and directing the fluid between any of a number of sources and destinations. Flexible tubing loops connected to select edges of the cassette may be received within peristaltic pump stations having rollers that press against the loops and rotate to move fluid through the cassette (and through the other components of the disposable circuit). An exemplary cassette is disclosed in U.S. Pat. No. 5,868,696, which is incorporated by reference herein in its entirety, although any suitable cassette may be used.

Figure 1:
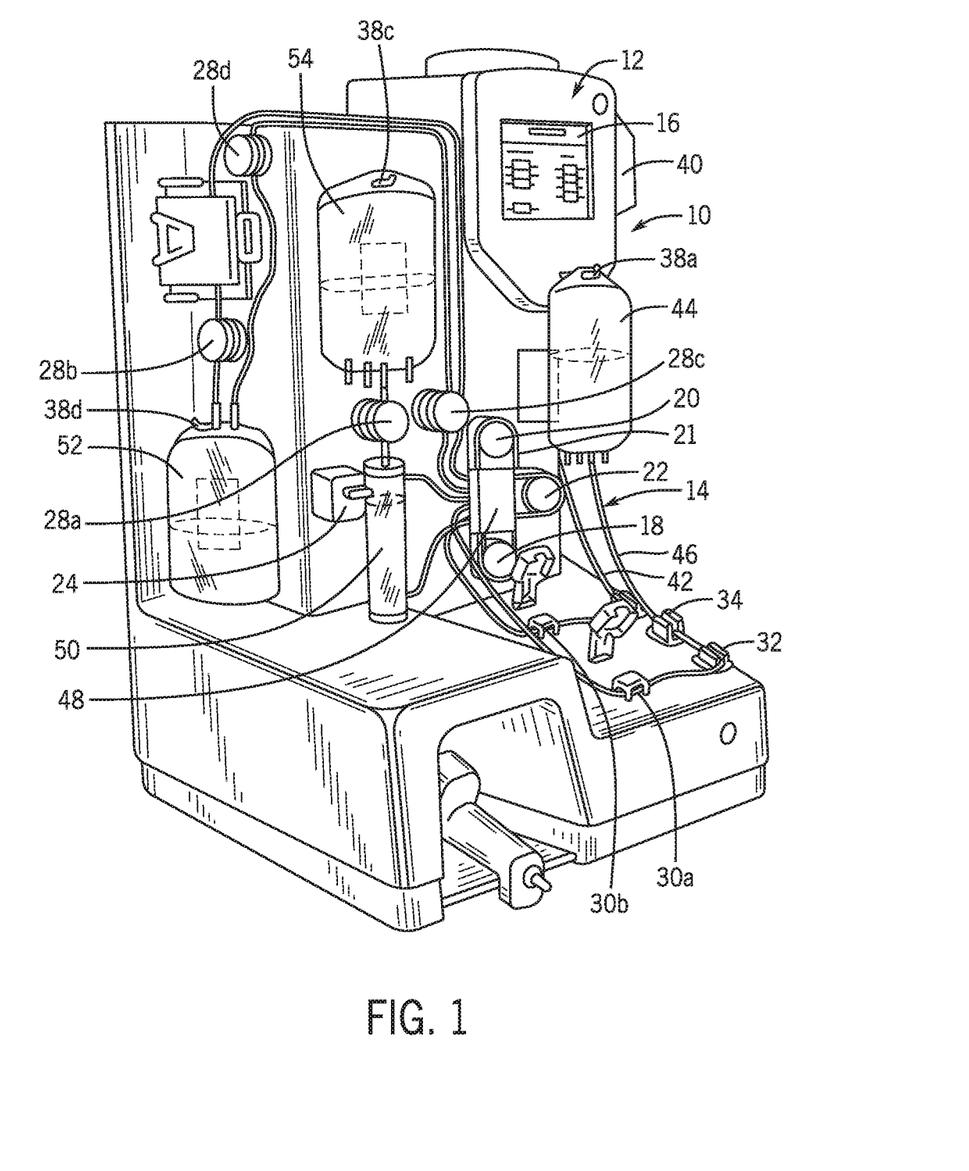
FIG. 1 is a perspective view of a blood processing system employing a durable processing device and a disposable fluid flow circuit, according to an exemplary embodiment.

FIG. 1 depicts a blood processing system, generally at 10, which includes a durable reusable processing device 12 and a disposable fluid flow circuit 14 for processing collected whole blood. The illustrated blood processing device 12 includes associated pumps, valves, sensors, displays and other apparatus for configuring and controlling flow of blood and additive solution through the disposable circuit. The device and the processing may be directed by an internal controller that includes a programmable microprocessor automatically controlling the operation of the pumps, valves, sensors, etc.

The processing device 10 may include a user input and output touch screen 16, a pump station including a whole blood pump 18, an RBC pump 20 and an additive solution pump 22, blood separator mounting station and drive unit 24, tubing clamps 28a-28d, sterile connection or docking devices 30a, 30b, one or more tubing clamps 32, and hematocrit sensor 34. The processing device may also include hangers 38a-d, each associated with a weight scale, for suspending the various containers of the disposable fluid circuit.

The fluid flow circuit 14 may include an additive solution container 40 and associated fluid flow tubing 42 for withdrawing the additive solution, a whole blood container 44 and associated fluid flow tubing 46 for withdrawal of collected whole blood from the container, and a processing module that includes pump cassette 48, separator 50 (e.g., spinning membrane separator, separation chamber placed within a centrifuge), red blood cell (RBC) container 52, plasma container 54, and associated connecting tubing. The pump cassette 48 may route the fluid flow through tubing loops 21 that extend from the cassette, and each loop may be uniquely positioned to engage a particular one of the pumps 18, 20, and 22. The tubing may extend through the cassette or the cassette may have pre-formed fluid flow paths that direct the fluid flow.

Figure 2A:
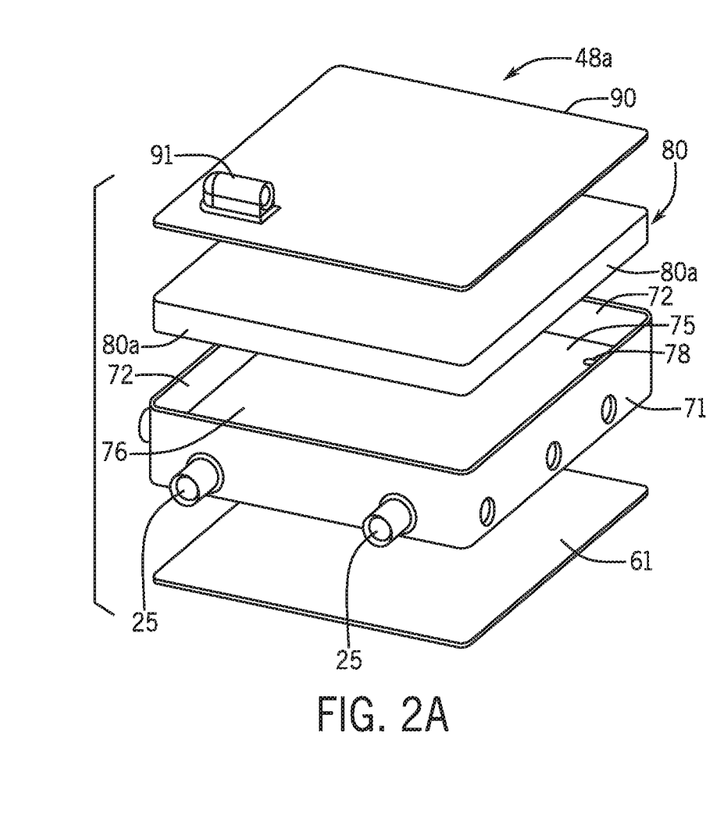
FIGS. 2A and 2B are top and bottom perspective views of various components of a cassette having an integrated leukoreduction filter, according to an exemplary embodiment.
Figure 2B:
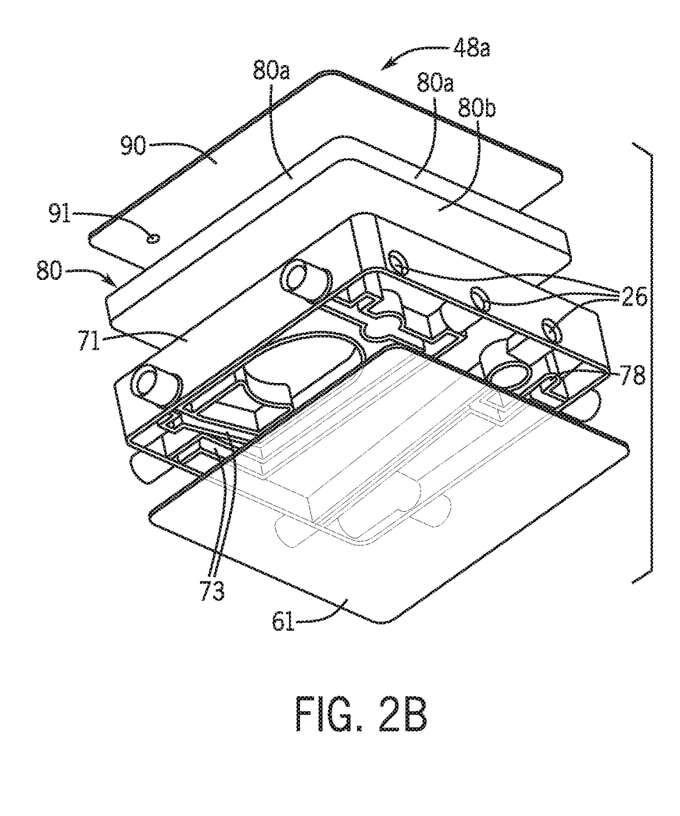

FIGS. 2A and 2B show top and bottom perspective views of the different components of one embodiment of a cassette 48a having an integrated leukoreduction filter. A rigid cassette body 71 may comprise a plurality of defined fluid passageways 73 in communication with ports 25 and 26 accessible from the outside the cassette 48a. The rigid cassette body 71 and its passageways 73 may be formed by plastic injection molding methods, although any suitable material and/or manufacturing methods may be used. A flexible sheeting or diaphragm 61 may cover the "bottom" of the cassette body 71, referring to the side of the cassette body 71 facing the durable equipment 12 of FIG. 1. The flexible sheeting 61 may be made of any suitable flexible material, such as PVC foil, amenable to be pressed by valve actuators of the durable equipment 12, allowing control of which of the fluid passageways 73 are open, closed, and/or connected to each other.

Referring to FIG. 2A, a rigid component 75 may serve to divide the bottom portion of the cassette body 71 comprising the fluid passageways 73 and the top portion of the cassette body 71 forming a receptacle 76 for a leukofilter medium 80 to fit therewithin. The rigid component 75 may be made by the same method, e.g., plastic injection molding, as the cassette body 71, although any suitable material and/or manufacturing methods may be used. Within the receptacle 76 may be fitted a leukofilter medium 80 adapted to remove or reduce the number of leukocytes from the fluid to be filtered. The fluid to be filtered, e.g., red blood cell suspension, may enter the receptacle 76 through an inlet port 78 in communication with one or more of the fluid passageways 73 underneath the rigid component 75 of the cassette body 71. The leukofilter medium 80 may be sealed hermetically at its edges 80a to the receptacle walls 72 formed by the cassette body 71 to ensure that the fluid to be filtered passes through the leukofilter medium 80. The leukofilter medium 80 may alternatively or additionally be sealed hermetically at its surface 80b (FIG. 2B) to the rigid component 75 of the receptacle 76. An embodiment in which the leukofilter medium is disposed substantially above or below the plane of the defined fluid passageways (substantially same x/y-position and different z-position) may be described as a stacked configuration.

The leukofilter medium 80 may be formed of any suitable material but, in one exemplary embodiment, may be formed of a melt-blown, nonwoven, fibrous material, such as a polybutylene terephthalate ("PBT") material. The leukofilter medium 80 may be formed from a single or a plurality of layers, which may be either substantially identical or differently configured. For example, a multi-layer leukofilter layer may be comprised of a plurality of fibrous layers, a plurality of non-fibrous layers, and/or a combination of fibrous layers and non-fibrous layers. Examples of various leukifiltration media are disclosed in US Patent Application Publication Nos. 2015/0265758, 2015/0265954, and 2015/0265755, which are incorporated by reference in their entireties, although any suitable leukofiltration medium may be used.

A hard, rigid, or semi-rigid component 90 may cover or enclose the "top" of the cassette body 71, referring to the side of the cassette body 71 facing away from the durable equipment 12 of FIG. 1. The component 90 may enclose or contain the leukofilter medium 80 within the receptacle 76 of the cassette body 71, sealing the medium 80 within the receptacle 76. The component 90 may comprise an outlet port 91 in communication with the filtrate leaving the leukofilter medium 80.

Figure 3A:
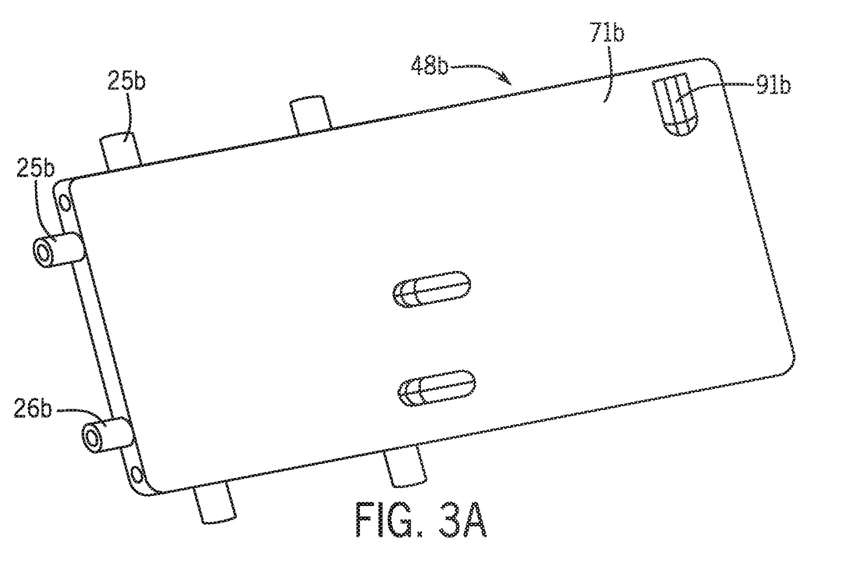
FIGS. 3A and 3B are top and bottom perspective views of a cassette having an integrated leukoreduction filter disposed substantially lateral to the cassette's defined fluid passageways, according to an exemplary embodiment.
Figure 3B:
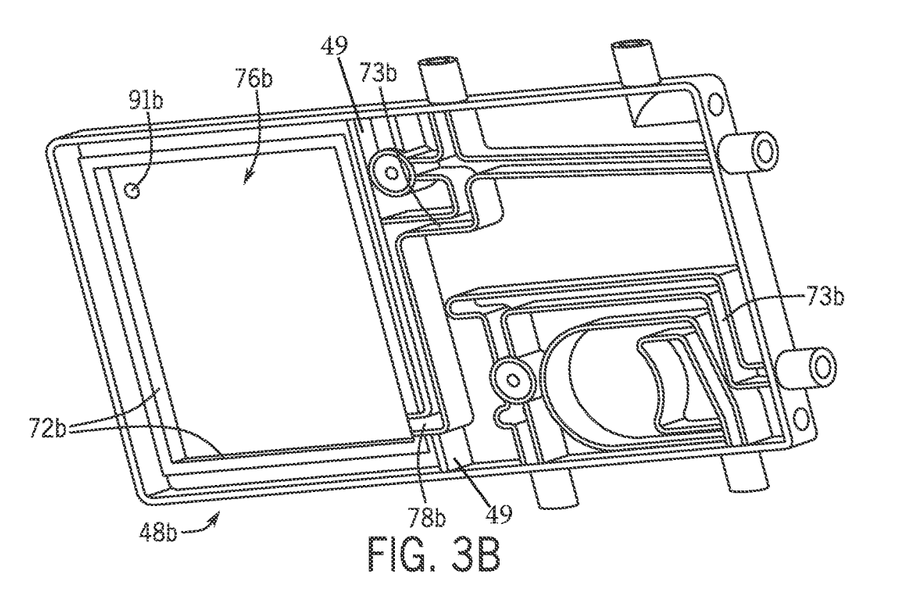

FIGS. 3A and 3B show an alternate embodiment of a cassette 48b having an integrated leukoreduction filter disposed substantially lateral to the defined fluid passageways. The embodiment in which the leukofilter is disposed substantially lateral to the plane of the defined fluid passageways (substantially same z-position and different x/y-position) may be described as a lateral configuration. FIG. 3A shows the top of the cassette 48b, and FIG. 3B shows the bottom of the cassette 48b. A rigid cassette body 71b may comprise a plurality of defined fluid passageways 73b in communication with ports 25b and 26b accessible from the outside the cassette 48b. The rigid cassette body 71b may also form a receptacle 76b lateral to the plurality of defined fluid passageways 73b, with the receptacle 76b separated from all of the defined fluid passageways 73b by a partition 49 extending orthogonally from an edge of the cassette body 71b to an opposite edge of the cassette body 71b (FIGS. 3B and 3O). The receptacle 76b may be configured to receive a leukofilter medium such as the medium 80 described above. Such as described with regard to FIGS. 2A and 2B, the rigid cassette body 71b, its passageways 73b, and the receptacle 76b may be formed by plastic injection molding methods, although any suitable material and/or manufacturing methods may be used.

The fluid to be filtered, e.g., red blood cell suspension, may enter the receptacle 76b through an inlet port 78b (see FIG. 3B) in communication with one or more of the fluid passageways 73b of the cassette body 71b. As described in connection with FIGS. 2A and 2B, the leukofilter medium may be sealed hermetically at its edges to the receptacle walls 72b formed by the cassette body 71b to ensure that the fluid to be filtered does not escape through or between the edges of the medium and the receptacle walls 72b. The inlet port 78b may be disposed slightly below the receptacle 76b in a z-axis direction closer to the durable equipment 12 of FIG. 1 to avoid the seal between the leukofilter medium and the receptacle walls 72b. The top of the cassette body 71b proximate to the receptacle 76b may comprise an outlet port 91b in communication with the filtrate leaving the leukofilter medium.

Figure 3C:
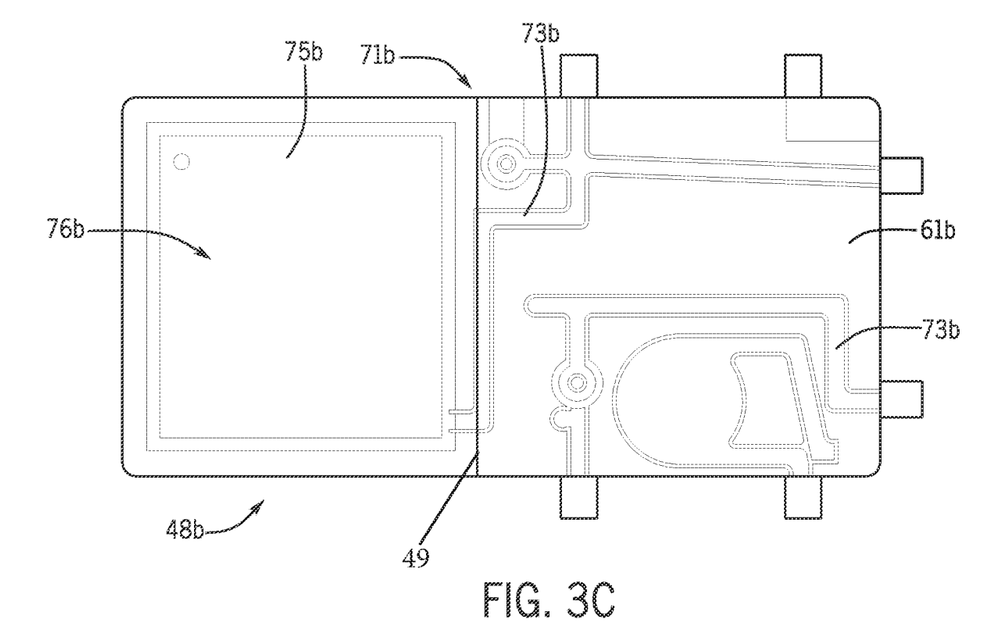
FIG. 3C is a bottom perspective view of the cassette in FIGS. 3A and 3B having covers disposed on the bottom of the cassette body, according to an exemplary embodiment.

FIG. 3C shows the bottom of the cassette 48b having sheetings 61b and 75b disposed on the bottom of the cassette body 71b. The flexible sheeting 61b may be made of the same flexible material, e.g., PVC foil, as sheeting 61 in FIGS. 2A and 2B, amenable to be pressed by valve actuators of the durable equipment 12, allowing control of which of the fluid passageways 73 are open, closed, and/or connected to each other. The sheeting 75b enclosing the receptacle 76b may be comprised of the same material as flexible sheeting 61b or may be comprised of a rigid material, such as that of the cassette body 71b. In an embodiment in which the sheetings 75b and 61b are comprised of the same material, the sheetings may be formed from a single sheet of material covering both the defined passageways 73b and the receptacle 76b, or the sheetings may be formed from different sheets of material.

In an event in which the particles, e.g., red blood cells, retained by the filter medium become saturated within the medium and the medium is no longer passable by fluid, it may be desirable to have a bypass mechanism so that fluid does not have to pass through the medium in order for the fluid procedure to continue. It may also be desirable to have a bypass mechanism for when reverse flow is desired without filtrate that has just passed through the medium going backwards into the filter medium.

Figure 4:
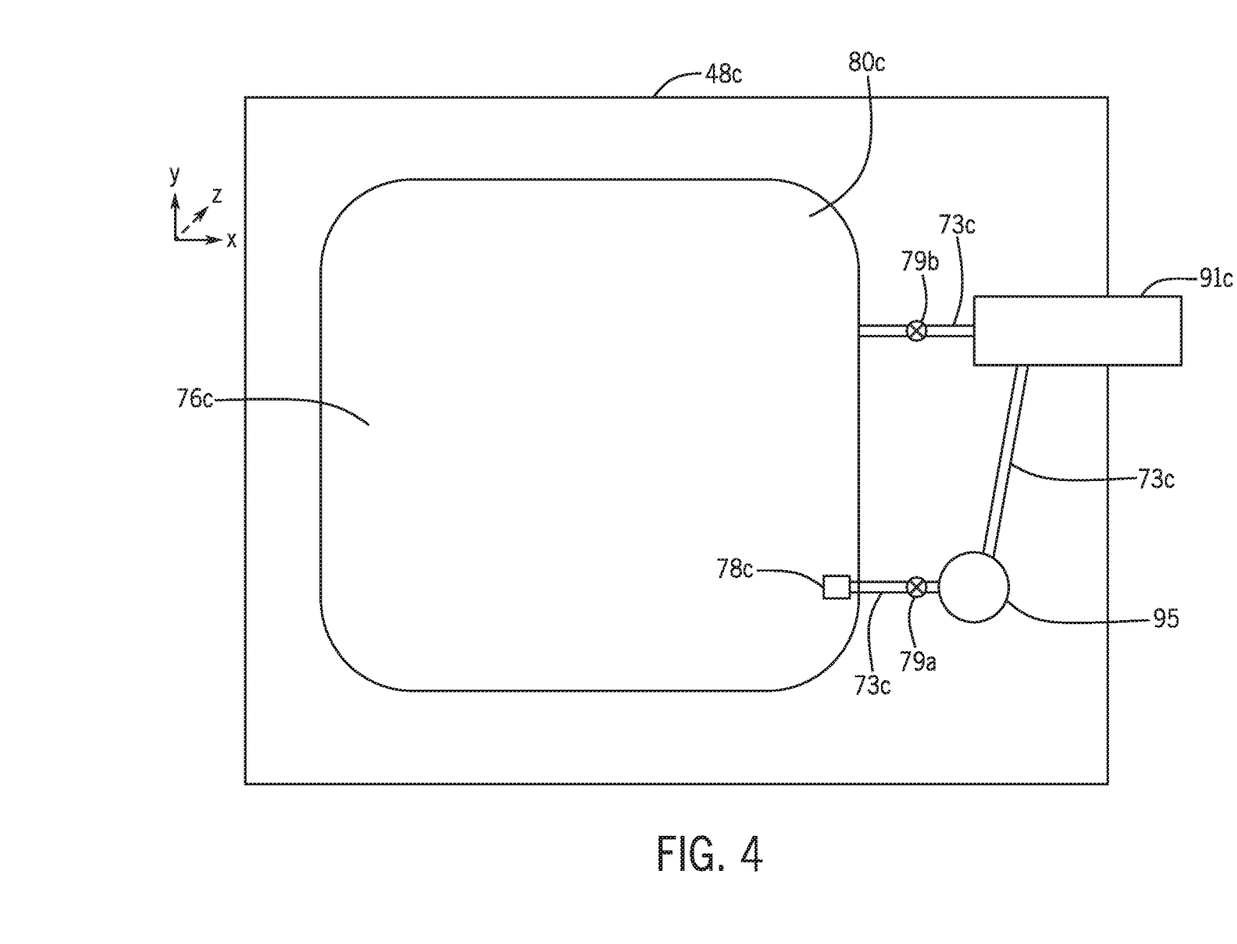
FIG. 4 is a schematic diagram of a cassette having an integrated leukoreduction filter and an integrated bypass mechanism, according to an exemplary embodiment.

Turning to FIG. 4, a schematic diagram is shown of one embodiment of a cassette having an integrated leukoreduction filter and an integrated bypass mechanism. The embodiment of FIG. 4 shows a cassette 48c having a filter medium 80c disposed in a stacked configuration, similar to the configuration shown in FIGS. 2A and 2B. In one embodiment, the defined fluid passageways may be disposed on a plane closer to the durable equipment 12 (FIG. 1) than that of the filter medium 80c. The fluid to be filtered, e.g., red blood cell suspension, may enter a receptacle 76c housing the filter medium 80c through an inlet port 78c in communication with one or more of the fluid passageways. The inlet port 78c may also be in communication with a bypass 95, which in turn, may be in communication with an outlet port 91c, which is also in communication with the filtrate of the filter medium 80c. A valve 79a may be disposed between the inlet port 78c and the bypass 95 to control direction of fluid flow. The valve 79a may be open or closed, depending on whether it is desired for fluid to enter receptacle 76d through inlet port 78c or for fluid to bypass the filter medium 80c by entering bypass 95 and out of the cassette 48c via outlet port 91c. The bypass mechanism may be activated by opening valve 79a. Once valve 79a is open, fluid entering the inlet port 78c may be directed to the bypass 95 rather than the filter medium due to bypass 95 providing the pathway of less resistance than the pathway through the filter medium. A second valve 79b may optionally be disposed between the outlet port 91c and the receptacle 76c containing the filtrate. When flow coming out of outlet port 91c needs to be reversed, filtrate that has just left the filter medium 80c may be reversed into the cassette 48c by closing valve 79b and opening valve 79a. Due to the tendency of fluid to flow in the path of least resistance, fluid being reversed into the cassette 48c will tend to flow from the outlet port 91c to the bypass 95 rather than back into the filter medium 80c even without the presence of valve 79b, but valve 79b may optionally be incorporated into the cassette 48c as a failsafe. Valve 79b may be disposed along a passageway 73c in communication between filter medium 80c and the outlet port 91c. The passageway 73c may be disposed at an xiy-position substantially not overlapping with the x/y- position of the filter medium 80c to accommodate room in the cassette for a bypass mechanism.

Figure 5:
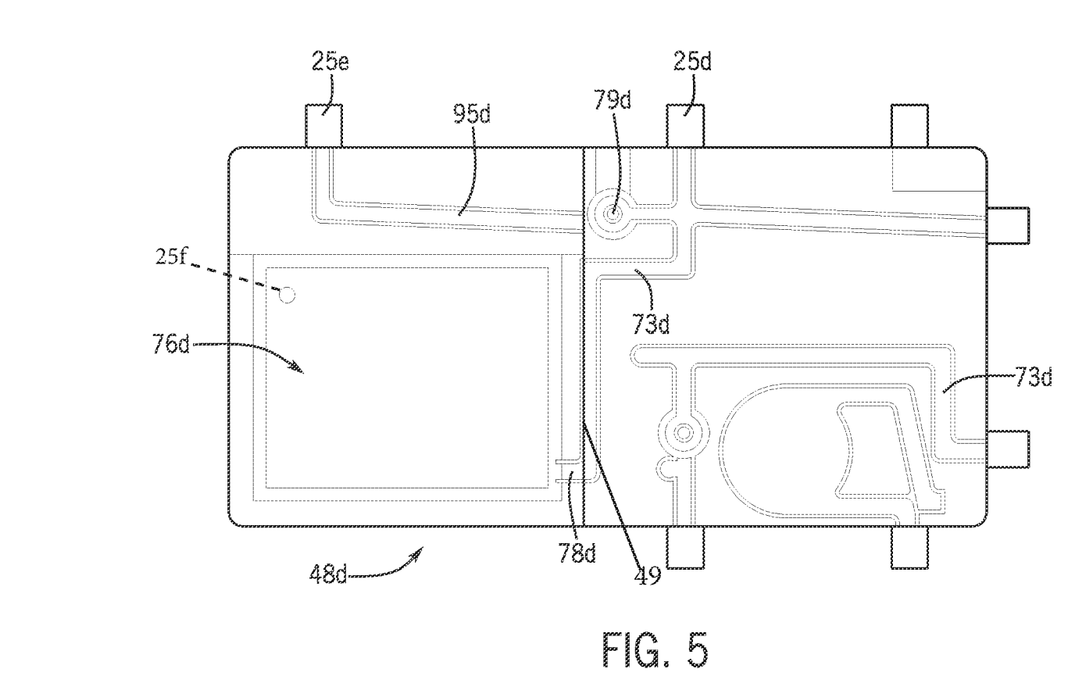
FIG. 5 is a bottom perspective view of a cassette having an integrated leukoreduction filter and an integrated bypass mechanism, according to another exemplary embodiment.

FIG. 5 shows an alternate embodiment of a cassette having an integrated leukoreduction filter and an integrated bypass mechanism. The embodiment of FIG. 5 shows a cassette 48d having a receptacle 76d configured to receive a filter medium (not illustrated) disposed in a lateral configuration at substantially the same plane as the defined fluid passageways 73d, with the receptacle 76d shown in FIG. 5 as being separated from the defined fluid passageways 73d by a partition 49 (as in the embodiment of FIGS. 3A-3O). The fluid to be filtered, e.g., red blood cell suspension, may enter the receptacle 76d housing the filter medium through an inlet port 78d in communication with one or more of the fluid passageways underneath the filter medium and may exit the receptacle 76d through an outlet port 25f. The inlet port 78d may be in communication with a cassette inlet port 25d, into which fluid to be filtered may enter. The cassette inlet port 25d may be in communication with a valve 79d, which may be open or closed, depending on whether it is desired for fluid to enter receptacle 76d through inlet port 78d or for fluid to bypass the filter medium by entering bypass passageway 95d and out of the cassette 48d via cassette outlet port 25e. The bypass mechanism may be activated by opening valve 79d. Once valve 79d is open, fluid entering the inlet port 25d may be directed to the bypass 95d rather than the filter medium due to bypass 95d providing the pathway of less resistance than the pathway through the filter medium.

Without limiting the foregoing description, in accordance with a first aspect of the subject matter herein, there is provided a fluid processing system for controlling fluid flow. The system includes a cassette comprising defined passageways within a first portion of the cassette and a filter receptacle within a second portion of the cassette. An inlet port is in communication with one or more of the defined passageways and an inlet side of the filter receptacle. An outlet port is in communication with an outlet side of the filter receptacle, and a filter medium is within the filter receptacle between the inlet port and outlet port.

In accordance with a second aspect which may be used or combined with the immediately preceding aspect, the filter medium is a leukoreduction filter.

In accordance with a third aspect which may be used or combined with any of the preceding aspects, the first and second portions of the cassette are disposed laterally to each other in substantially the same plane.

In accordance with a fourth aspect which may be used or combined with any of the preceding aspects, the first and second portions of the cassette are disposed generally parallel to one another within substantially different planes.

In accordance with a fifth aspect which may be used or combined with any of the preceding aspects, the inlet port is disposed closer in a z-axis direction relative to the filter receptacle and relative to the outlet port to a durable hardware supporting the cassette.

In accordance with a sixth aspect of the subject matter herein, there is provided a fluid processing system for controlling fluid flow. The system comprises a cassette comprising defined passageways within a first portion of the cassette and a filter receptacle within a second portion of the cassette. An inlet port is in communication with one or more of the defined passageways and an inlet side of the filter receptacle. A first outlet port is in communication with an outlet side of the filter receptacle. A filter medium is disposed within the filter receptacle between the inlet port and the first outlet port. A bypass passageway is in communication with the inlet port and a second outlet port, and fluid flowing through the bypass passageway does not make contact with the filter medium.

In accordance with a seventh aspect which may be used or combined with the immediately preceding aspect, the first and second outlet ports comprise the same port.

In accordance with an eighth aspect which may be used or combined with the sixth or seventh aspect, the first and second outlet ports comprise different ports.

In accordance with a ninth aspect which may be used or combined with any of the preceding aspects, the filter medium is a leukoreduction filter.

In accordance with a tenth aspect which may be used or combined with any of the preceding aspects, the first and second portions of the cassette are disposed laterally to each other in substantially the same plane.

In accordance with an eleventh aspect which may be used or combined with any of the preceding aspects, the first and second portions of the cassette are disposed generally parallel to one another within substantially different planes.

In accordance with a twelfth aspect which may be used or combined with any of the preceding aspects, the inlet port is disposed closer in a z-axis direction relative to the filter receptacle and relative to the first outlet port to a durable hardware supporting the cassette.

In accordance with a thirteenth aspect which may be used or combined with the tenth aspect, a valve is disposed between the inlet port and the bypass passageway.

In accordance with a fourteenth aspect which may be used or combined with the thirteenth aspect, a valve is disposed between the inlet port and the bypass passageway.

In accordance with a fifteenth aspect which may be used or combined with the tenth through fourteenth aspects, a valve is disposed between the inlet port and the bypass passageway.

In accordance with a sixteenth aspect which may be used or combined with the eleventh through fifteenth aspects, a valve is disposed between the first outlet port and the filter receptacle.

In accordance with a seventeenth aspect of the subject matter herein, there is provided a method for transferring fluid through a fluid flow path. The method comprises providing a cassette comprising defined passageways within a first portion of the cassette and a filter receptacle within a second portion of the cassette. An inlet port is in communication with one or more of the defined passageways and an inlet side of the filter receptacle. A first outlet port is in communication with an outlet side of the filter receptacle. A filter medium is disposed within the filter receptacle between the inlet port and the first outlet port. A bypass passageway is in communication with the inlet port and a second outlet port, and fluid flowing through the bypass passageway does not make contact with the filter medium.

In accordance with an eighteenth aspect which may be used or combined with the immediately preceding aspect, the filter medium is formed of a melt-blown, nonwoven, fibrous material.

In accordance with a nineteenth aspect which may be used or combined with the seventeenth and eighteenth aspects, the filter medium is sealed hermetically at its edges to walls of the filter receptacle.

In accordance with a twentieth aspect which may be used or combined with the seventeenth through nineteenth aspects, the cassette and the defined passageways are formed by plastic injection molding.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A cassette comprising:
   a cassette body comprising defined passageways, a filter receptacle, and a partition extending orthogonally from an edge of the cassette body to an opposite edge of the cassette body, with the partition separating all of the defined passageways from the filter receptacle;
   an inlet port to the filter receptacle defined in the partition and in communication with one or more of the defined passageways and an inlet side of the filter receptacle;
   an outlet port in communication with an outlet side of the filter receptacle; and
   a filter medium disposed within the filter receptacle between the inlet port and outlet port.

2. The cassette of claim 1, wherein the filter medium is a leukoreduction filter.

3. The cassette of claim 2, wherein the leukoreduction filter is sealed hermetically to the filter receptacle.

4. The cassette of claim 1, wherein the defined passageways and the filter receptacle are disposed laterally to each other in substantially the same plane.

5. The cassette of claim 4, wherein
   the inlet port is configured to direct fluid flow within the plane in which the defined passageways and the filter receptacle are disposed, and
   the outlet port is configured to direct fluid flow out of the plane in which the defined passageways and the filter receptacle are disposed.

6. The cassette of claim 1, wherein the cassette body further comprises a bypass passageway disposed on the same side of the partition as the filter receptacle.

7. The cassette of claim 6, further comprising a valve associated with one of the defined passageways, configured to be opened to direct fluid flow from said one of the defined passageways to the bypass passageway, and configured to be closed to direct fluid flow from said one of the defined passageways to the inlet port.

8. The cassette of claim 7, further comprising a location between the filter receptacle and the valve into which fluid flow is directed prior to fluid flow being directed into the bypass passageway or into the filter receptacle.

9. The cassette of claim 7, wherein the valve is spaced from the inlet port and the outlet port.

10. The cassette of claim 6, wherein
    the bypass passageway includes an outlet port,
    the defined passageways, the filter receptacle, and the bypass passageway are configured to direct fluid flow within the same plane, and
    the outlet port of the bypass passageway is configured to direct fluid flow out of the bypass passageway within said plane.

11. The cassette of claim 6, wherein
    the bypass passageway includes an outlet port,
    the defined passageways, the filter receptacle, and the bypass passageway are configured to direct fluid flow within the same plane, and
    the outlet port of the bypass passageway is configured to direct fluid flow out of the bypass passageway and out of said plane.

12. A method for transferring fluid through a cassette comprising a cassette body comprising defined passageways, a filter receptacle, a bypass passageway in communication with one or more of the defined passageways, and a partition extending orthogonally from an edge of the cassette body to an opposite edge of the cassette body, with the partition separating all of the defined passageways from the filter receptacle, the method comprising:
    directing fluid through at least one of the defined passageways;
    opening a valve to direct at least a portion of the fluid into the bypass passageway when said at least a portion of the fluid is not to make contact with a filter medium disposed within the filter receptacle; and
    closing the valve to direct at least a portion of the fluid into the filter receptacle and not into the bypass passageway when said at least a portion of the fluid is to make contact with the filter medium disposed within the filter receptacle.

13. The method of claim 12, further comprising directing said at least a portion of the fluid out of the bypass passageway via an outlet port, wherein
    the defined passageways, the filter receptacle, and the bypass passageway are disposed in substantially the same plane, and
    said outlet port directs said at least a portion of the fluid out of the bypass passageway within said plane.

14. The method of claim 12, further comprising directing said at least a portion of the fluid out of the filter receptacle via an outlet port, wherein
    the defined passageways, the filter receptacle, and the bypass passageway are disposed in substantially the same plane, and
    said outlet port directs said at least a portion of the fluid out of the filter eceptacle and out of said plane.

15. The method of claim 12, wherein the bypass passageway is disposed on the same side of the partition as the filter receptacle.

16. The method of claim 12, wherein fluid flowing into the filter receptacle is directed through the partition.

17. The method of claim 12, further comprising directing the fluid to a location between the filter receptacle and the valve prior to said at least a portion of the fluid being directed into the bypass passageway or into the filter receptacle.

18. The method of claim 12, wherein the valve is spaced from an inlet port and an outlet port of the filter receptacle.

19. The method of claim 12, wherein the filter medium is a leukoreduction filter.

20. The method of claim 19, wherein the leukoreduction filter is sealed hermetically to the filter receptacle.

* * * * *